(12) United States Patent
Feine (10) Patent No.: US 7,150,629 B2
(45) Date of Patent: Dec. 19, 2006

(54) LIGHTED ULTRASONIC HANDPIECE AND COLOR CODE GRIP SYSTEM

(76) Inventor: James Feine, P.O. Box 2009, Bellaire, TX (US) 77402

(*) Notice: Subject to any disclaimer, the term of this patent is extended or adjusted under 35 U.S.C. 154(b) by 424 days.

(21) Appl. No.: 10/249,165

(22) Filed: Mar. 19, 2003

(65) Prior Publication Data

US 2004/0185412 A1  Sep. 23, 2004

(51) Int. Cl.
*A61C 3/00* (2006.01)
*A61C 1/07* (2006.01)

(52) U.S. Cl. ........................ 433/119; 433/86

(58) Field of Classification Search ............... 433/119, 433/29, 86
See application file for complete search history.

(56) References Cited

U.S. PATENT DOCUMENTS

| 4,012,647 | A | * | 3/1977 | Balamuth et al. | 310/317 |
| 4,578,033 | A | * | 3/1986 | Mossle et al. | 433/29 |
| 5,423,677 | A | * | 6/1995 | Brattesani | 433/72 |
| 5,868,563 | A | * | 2/1999 | Davis et al. | 433/29 |
| 5,899,692 | A | * | 5/1999 | Davis et al. | 433/80 |
| 6,029,304 | A | * | 2/2000 | Hulke et al. | 15/105 |
| 6,164,968 | A | * | 12/2000 | Feine | 433/119 |
| 6,208,788 | B1 | * | 3/2001 | Nosov | 385/121 |
| 6,328,566 | B1 | * | 12/2001 | Feine | 433/119 |
| 6,386,866 | B1 | * | 5/2002 | Hecht et al. | 433/29 |
| 6,503,081 | B1 | * | 1/2003 | Feine | 433/119 |

* cited by examiner

*Primary Examiner*—Cris L. Rodriguez
*Assistant Examiner*—Candice C. Stokes
(74) *Attorney, Agent, or Firm*—Daniel N. Lundeen; Lundeen & Dickinson, LLP (57) ABSTRACT

The present invention relates to a dental scaling translucent insert which provides a coaxially aligned light adjacent the distal end of such insert for illuminating the tip of the dental scaler which light may be provided by light emitting from a fiber optic light guide from a light source located remotely from the tip. The light provided can also be used to view through a camera lens system located in translucent insert to provide a clear unobstructed view of the work at the tip of the scaler on a remote screen or for recording.

38 Claims, 5 Drawing Sheets

LIGHTED ULTRASONIC HANDPIECE AND COLOR CODE GRIP SYSTEM

BACKGROUND OF INVENTION

The present invention relates to a medical or dental handpiece; specifically to an ultrasonic handpiece providing a independently controlled light source connected through an interchangeable and easily identifiable grip on an ultrasonic insert adjacent the end of the handpiece for illuminating the surface to be engaged by the tip of the handpiece and which may additionally provide a camera lens for viewing the work area without interference with the work performed.

The present invention relates to an ultrasonic tool, which can be a dental scaler, or alternatively a scalpel, additionally providing a light directed from the handpiece of the tool toward the work surface on which the tip or blade is engaged. For ease of description, applicant discloses the dental scaling embodiment, but an ultrasonic scalpel can be fabricated from the present disclosure without departure from the coverage of this application.

Light emission from an operator's handpiece allows the operator a clear and unobstructed lighted surface on which the dental scaling tip works. This permits the operator of the scaling tip to readily see the teeth and gums or dental appliances (i.e. implants, crowns, bridges or the like) while using the ultrasonic dental scaler. Heretofore, light from an outside source such a pole mounted dental light or headlamp system shines in the back of the working area and is blocked from the working area by the hand or body of the operator or by the patient's body, tongue, or teeth. Light directed from a distal edge of the handpiece will provide the necessary illumination directly onto the working area without shadows or other impediments. Although various prior art devices disclosed mounting a light or light source in the handpiece, so far as known to applicant, no prior art provides a light path through the insert grip to guide remotely generated light to the tip of the scaler. This provides features not heretofore available in the industry. For example, the presence of a bulb in the handpiece is eliminated thereby eliminating the heat associated with this proximal light source.

Each insert tip is retained in a grip which provides a light guide which therefore remains in fixed spatial relationship with the tip to be illuminated. Since the light is driven by its own separate power supply, it may remain illuminated throughout the procedure and is not dependent upon the ultrasonic drive circuit to power the light required by other prior art devices. This feature allows the light to be used for viewing of the mouth of the patient and further allows the light to remain at a fixed intensity throughout the procedure despite variations in electrical power caused by the loading of the coil which energizes the ultrasonic stack, or piezoelectric crystal.

Since the power supply to the light source is separate and apart from the power supply to the coil in the magnetostrictive ultrasonic arrangement, there is no frequency distortion caused by the use or non-use of the lamp to interfere with the power harmonics of the coil. Finally, the inserts will always be useable with the conventional handpieces since the light source connection need not connected to a power supply to operate the magnetostrictive stack. Since the grip provides a light source, it may also provide a camera lens to capture the view of the work surface as the technician performs the necessary operation.

SUMMARY OF INVENTION

The present invention is a lighted ultrasonic insert providing a dental scaling tip or alternatively a scalpel, a velocity transducer connected to said tip, an ultrasonic stack connected to said velocity transducer inserted in a grip having a longitudinally aligned light guide from a light source remote from the magnetostrictive stack insert (or an alternative piezoelectric crystal oscillator), and a light conductor connected to said light source for guiding light from a remote light source to the distal end of said insert.

The improved lighted ultrasonic dental scaling insert features a scaling tip, a velocity transducer connected to said scaling tip, an ultrasonic stack connected to said velocity transducer inserted through a grip adapted for connection with a dental scaling handpiece of the present invention. An interchangeable grip sheath can be ergonomically form fitted to more easily allow the operator to grip the ultrasonic device for long periods of time without muscle fatigue or cramping. Additionally, the interchangeable grip sheath may be color coded to permit the operator to readily identify a preferred handpiece from amongst a number of similar designed handpieces. This ability to visually determine the instrument being accessed by virtue of the color coding and the ability to use an ergonomically designed sheath adaptable to the hand of the operator fosters a less stressful clinical setting for both the dental technician and the patient.

The light source terminus in the handpiece abuts the translucent grip body and is connected to a light transmission cable permitting the transmission through the terminus into the interior of the grip covered by the sheath. A light source, which may be switched on or off and regulated to increase or decrease light intensity through the light transmission cable provides illumination through cable to the light source terminus. As previously noted, an ergonomic resilient and opaque sheath is retained over the translucent grip body to permit comfortable use of the ultrasonic device and also blocks ambient light from escaping from the translucent grip at any point except the distal end of the grip adjacent the tip.

Alternatively, the lighted ultrasonic handpiece can provide a partially translucent grip body providing a longitudinal passage through which an ultrasonic velocity transducer is connected to a tip and energized by an ultrasonic generator driving a said handpiece having a light source terminus abutting said translucent grip body providing illumination through the grip body to a distal end of the grip body adjacent a tip and a light cable connected to said light source terminus providing illumination from a remote source to the light source terminus; and, a resilient ergonomic opaque sheath covering said grip thereby preventing the light from leaving the translucent grip body at any position except its distal tip. Since the sheath may be readily and easily slip on and off the grip, it can be colored to provide visual identification to the operator of the type and configuration of the tip and light system being utilized. This facilitates easy and quick use of a number of tips for busy dental hygienists who may prefer one tip over an alternate design for a given problem.

The ultrasonic handpiece grip system of the present invention can also be fashioned with a molded body having a longitudinal passage therethrough; and, a translucent insert, such as a fiber optic channel, to transmit light from the handpiece light terminus to the grip insert, which provides an exterior surface for engaging an elastomeric opaque sheath and further providing a passage for the insertion of a velocity transducer and water path to the distal tip of the grip system and permitting the passage of light through the interior of the molded body to the distal end of the grip body to illuminate the adjacent distal tip.

Additionally, the ultrasonic handpiece grip system of the present invention can be fashioned with a lens located at the distal end of the grip and an optical image transmission path for connection to a video or photographic viewing system mounted at a remote location.

DETAILED DESCRIPTION

The present invention relates to a dental scaling insert providing a translucent path from a light source to the end of the handpiece through a translucent grip covered by an ergonomically designed resilient sheath. In a preferred embodiment shown in FIG. 1, insert system I is comprised of a magnetostrictive stack 14 typically formed of nickel or nickel alloy plates in a manner well known to those skilled in this art, which are soldered together and which respond to electrical energy supplied by coil 19 encircling stack 14 in the handpiece H. Stack 14 is connected to a velocity transducer 16 which is connected to a scaling tip 18 and which is covered with grip 10. Grip 10 is formed from two segments or pieces of high grade plastic, for example, such as a polycarbonate, that provide a profile on their interior surface to retain the velocity transducer 16. In this embodiment, one or more teeth 13 are provided on the exterior lateral surfaces of the velocity transducer 16 to prevent rotation of the velocity transducer in the interior passage of the grip 10. Velocity transducer 16 may be integral with scaling tip 18 or may be threaded to provide threaded connection with scaling tip 18. Velocity transducer 16 provides a longitudinal pathway 26 for the delivery of water through port 24 in transducer 16 to scaling tip 18.

Figure 1:
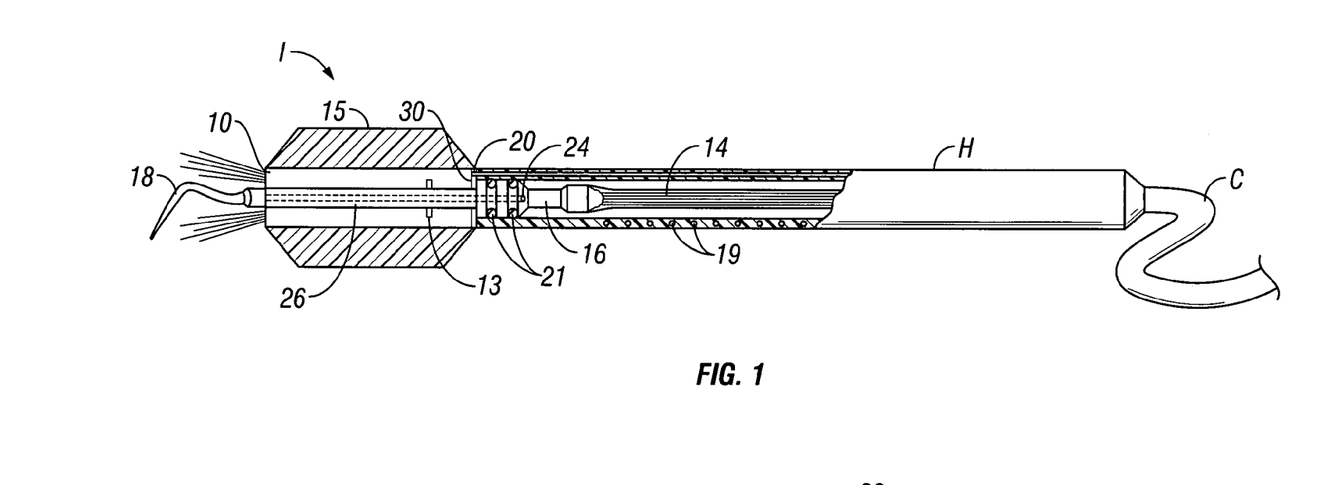
FIG. 1 is a partial cross-sectional perspective view of the dental scaling insert, grip and sheath of the present invention.

The handpiece H is connected with cable bundle C which provides the electrical connection to the remote power supply (not shown) to drive the magnetostrictive insert, a water supply to cool stack 14 and rinse the affected area in the patient's mouth or gum being cleaned through the water pathway 26, and to the light source by either fiber optic cabling FO or liquid light cabling (not shown).

Translucent grip 10 is annular and provides a light path for light provided at its proximal end 30 by light ring 20 to a distal end of grip 10 where the light emitted is adjacent the tip of dental scaler 18. Light ring 20 is positioned adjacent the proximal end of translucent grip 10 and retained there by a recessed lip 31 in handpiece H, as more closely described in FIG. 3. Insert 10 is compressively engaged in the handpiece H with one or more 0-rings 21 as more clearly shown in FIG. 3.

Figure 2:
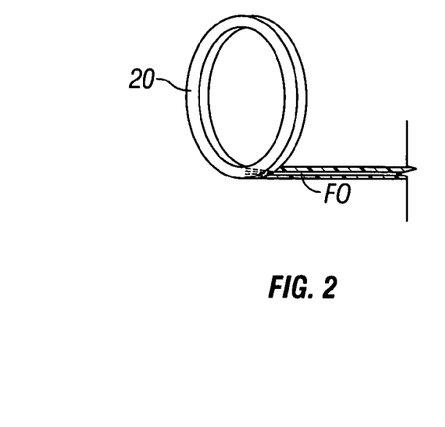
FIG. 2 is a side view perspective view of the light ring of the present invention.

FIG. 2 more clearly demonstrates a method of connecting a fiber optic cable FO to the light ring 20, which is held adjacent the proximal end 30 of the insert 10. The fiber optic cabling FO is splayed and the individual fibers are affixed to a lateral edge of the light ring 20. An epoxy can be used to attach the ends of the fiber optic FO individual fibers to the ring 20. An alternative embodiment of the light delivery system is disclosed in FIGS. 12 and 13.

Insert grip alone 10 is hard and difficult to hold over an extended period of time. Accordingly, a sheath 15 is engaged over the translucent grip 10 to provide a larger diameter material that is more readily conformable to the hand of the operator to reduce the fatigue associated with long extended treatment processes. This sheath can be manufactured using many types of sterilizable soft or semisoft materials such as silicon rubber. The color and hardness of the material of sheath 15 can be controlled during the manufacturing process or molding of the sheath by selection of appropriate color and durometer raw material for the fabrication of the sheath. The Color ID™ system of the applicant, as more fully described in U.S. Pat. No. 6,328,566, which is incorporated herein by reference as if fully copied herein, can be coordinated in this grip system to provide an easily identifiable system of scaling tip and shape to the dental hygienist.

Additionally, sheath 15 can be fabricated to provide a number of differing shapes of exterior surfaces to conform more ergonomically to the hand and preference of the dental hygienist. A variety of shapes will be more fully described herein. To retain sheath 15 on grip 10, the exterior surface of grip 10 can be roughened or ribbed 46 to provide resistance to movement of the sheath on the grip. Since sheath 15 is resilient, the operator will slip the desired shape and color on grip 10 and the roughened or ribbed exterior surface 46 of the grip will allow sheath 15 to remain fixed on grip 10 without substantial movement.

Sheath 15 can also be installed by slipping it over other manufacturer's ultrasonic inserts to give the operator the ability to use the Color ID™ system to identify the insert for the hygienist. Since sheath 115 can be readily slipped on and off the grip 10 of the present invention, any number of differing color schemes and shapes may be used by the operator to suit the operator's preferences. The sheath may be marketed in assorted packages or ordered in one preferred color and style as the hygienist prefers. Once received the sheaths may be inserted over the grip 10, sterilized and used by the hygienist.

Figure 11:
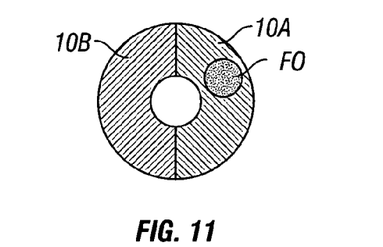
FIG. 11 is a cross-sectional end view of the segmented insert fabricated with a fiber optic pathway to transmit light from the light ring to the distal end of the insert.

As may be readily appreciated from FIG. 11, grip 10 can be fabricated to also provide a similar path for a light guide in the form of a fiber optic bundle. The use of a remote light source and control circuit eliminates the need for a light emitting diode or incandescent bulb in the grip or handpiece, but still allows the light to remain on without power being used in the scaler tip. The remote control circuit contains a heat sink, miniaturized ballast and ultrasonic generator circuitry (which can be either for driving a magnetostrictive or a piezoelectric device) and a circuit for powering and control a high intensity light system. An incandescent bulb, a quartz halogen arc or a high intensity light emitting diode lamp or any other high intensity light emission source may be adapted for use in the remotely located source and can be independently monitored by the circuitry of the remote control device which can provide an automatic shutoff after detection of either a period of inactivity of the ultrasonic circuitry or dangerous temperature build up in the lamp section, or both. A rheostat can also be provided in the remote power supply to adjust the level of intensity of the light delivered to the distal tip end of the ultrasonic device. Each of these enhancements are readily accomplished by a person having ordinary skill in this art field. Since the light source is operated independent of the dental scaling handpiece, the control may also provide means for permitting the attachment of a headlamp for the use of the operator. Light is delivered to the handpiece H by either a fiber optic cable bundle FO, or by a liquid light guide cable (not shown), such as may be obtained from Rofin Australia Pty, Ltd., for example. Additionally, as more fully described subsequently in this application, an alternative embodiment can be provided with a lens and cable connection affixed in the grip to permit imaging of the process at the tip of the dental scaler.

Figure 3:
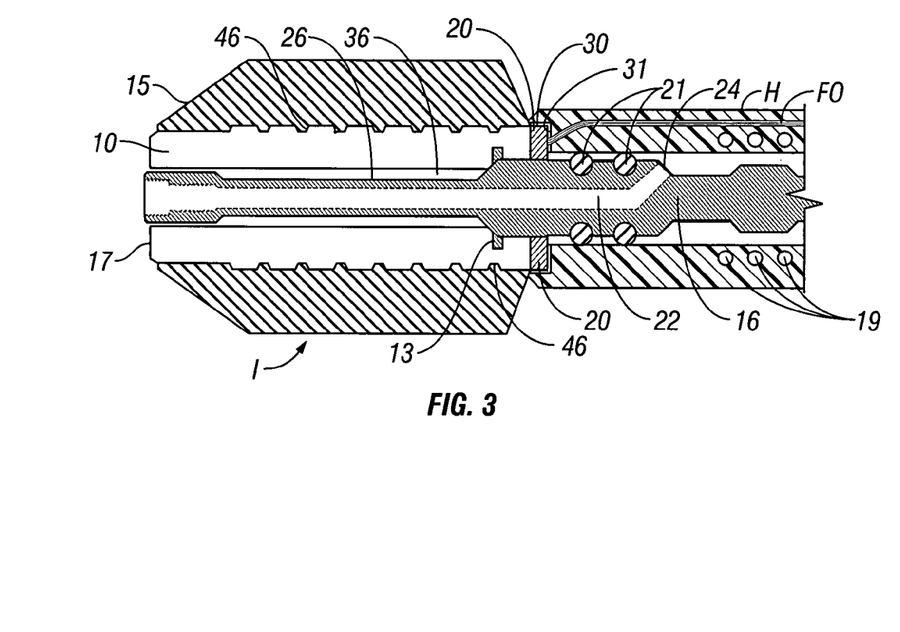
FIG. 3 is a cross-sectional side view of the grip and sheath on the insert with the light ring and handpiece of the present invention.

FIG. 3 discloses the perspective view of the light ring of the present invention showing light ring 20 connected to a multi-stranded fiber optic cable FO which runs through handpiece H of FIG. 1 with each of such fibers being attached to the exterior lateral surface of the light ring. Light ring 20 provides an outer diameter which fits inside a groove 31 provided in handpiece H adjacent the proximal end 30 of translucent insert or grip 10. The light from the light source reaches the light ring 20 and is diffused throughout the ring and thereby transmitted to the translucent insert or grip 10. The light is thereby transmitted through insert 10 to the exposed distal end of the insert system I to provide light to the work surface adjacent the tip 18. It will be readily appreciated by those skilled in the art that the transducer 16 and tip 18 can thus be made of a conventionally opticail opaque material such as metal, however, the light ring 20 and insert 10 encircle the transducer 16 and tip 18 to provide illumination. Sheath 15 covers the grip to allow the operator to comfortably hold the ultrasonic scaling device. FIG. 3 shows insert 10 with a threaded velocity transducer 16 to permit the interchange of scaling tips to the velocity transducer in an alternative manner.

Figure 4A:
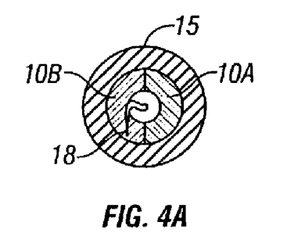
FIG. 4A is an end view of the cylindrical sheath around the translucent insert of the present invention.
Figure 4B:
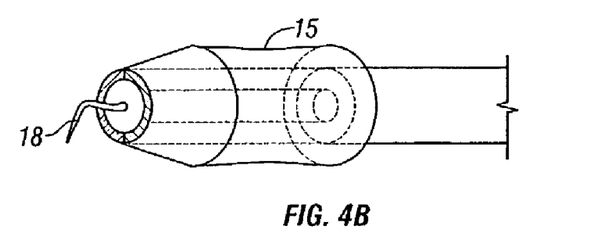
FIG. 4B is a perspective side view of the cylindrical sheath around the translucent insert of the present invention.

FIG. 4A is an end view of an alternative cylindrical form of sheath 15 mounted on conjoined inserts 10A and 10B which support scaling tip 18 on velocity transducer 16 (not seen in this view). FIG. 4B is a side view of the cylindrical sheath 15.

Figure 5A:
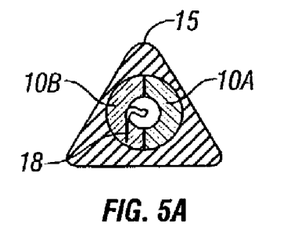
FIG. 5A is an end view of the triangular sheath around the translucent insert of the present invention.
Figure 5B:
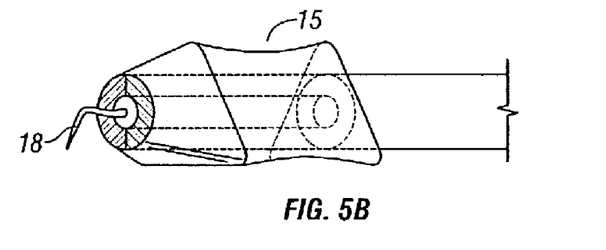
FIG. 5B is a perspective side view of the triangular sheath around the translucent insert of the present invention.

FIG. 5A is an end view of another alternative triangular form of sheath 15 mounted on the conjoined inserts 10A and 10B which support scaling tip 18 on velocity transducer 16. FIG. 5B is a side view of triangular sheath 15.

Figure 6A:
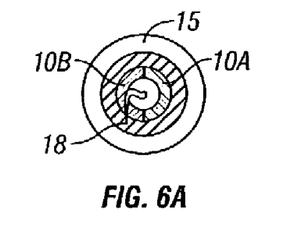
FIG. 6A is an end view of the tapered backed to front sheath around the translucent insert of the present invention.
Figure 6B:
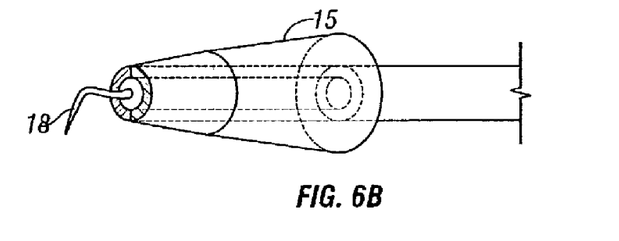
FIG. 6B is a perspective side view of the tapered back to front sheath around the translucent insert of the present invention.

FIG. 6A is an end view of another alternative tapered conical form of sheath 15 mounted on the conjoined inserts 10A and 10B which support scaling tip 18 on velocity transducer 16. FIG. 6B is a side view of the tapered conical form of sheath 15.

Figure 7A:
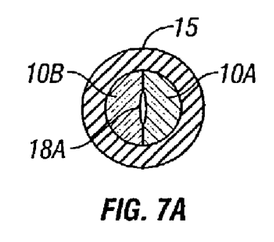
FIG. 7A is an end view of the concave sheath around the translucent insert of the present invention.
Figure 7B:
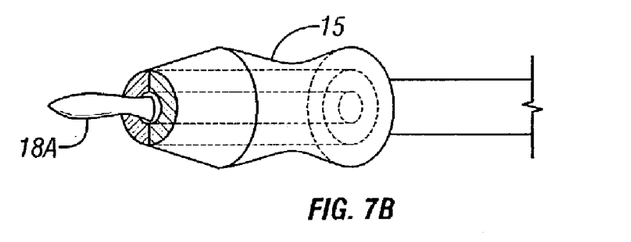
FIG. 7B is a perspective side view of the concave sheath around the translucent insert of the present invention, showing a scalpel tip.

FIG. 7A is an end view of another concave form of sheath 15 mounted on the conjoined inserts 10A and 10B mounting a scalpel blade 18A on the end of the velocity transducer. FIG. 7B is a side view of this form of sheath 15 showing the scalpel blade, which is an alternative use of the present invention.

Figure 8A:
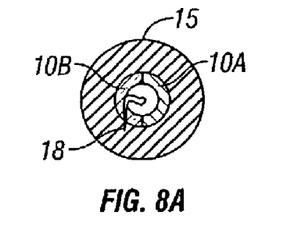
FIG. 8A is an end view of the alternative tapered front to back sheath around the translucent insert of the present invention.
Figure 8B:
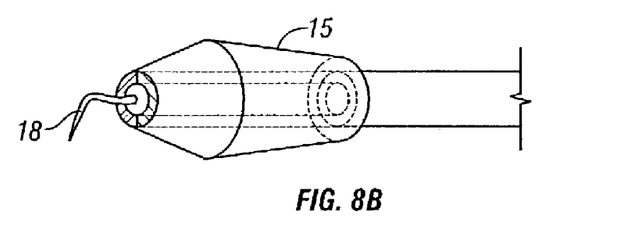
FIG. 8B is a perspective side view of the alternative tapered front to back sheath around the translucent insert of the present invention.

FIG. 8A is an end view of another view of a tapered conical form of sheath 15 showing a taper from large at the distal end to small at the proximal end. FIG. 8B is a side view of this alternative tapered conical form of sheath 15.

Figure 9:
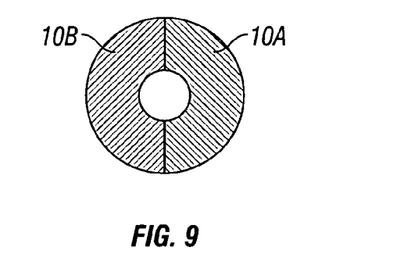
FIG. 9 is a cross-sectional end view of the segmented insert fabricated from two translucent halves.
Figure 10:
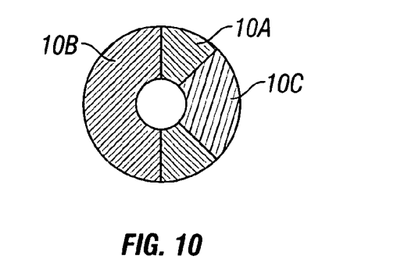
FIG. 10 is a cross-sectional end view of the segmented insert fabricated with a portion of one half of the insert translucent and the remaining portions opaque.

As previously noted, the insert system I of the present invention can provide a number of alternative arrangements which remain within the scope and intent of the present disclosure. For example, FIG. 9 shows an end view of two halves of the translucent polycarbonate insert body that are ultrasonically welded together to form insert 10. As previously noted, the interior surface of the two halves provides a profile to retain velocity transducer 16. Alternatively, as shown in FIG. 10, a portion of one half of insert 10 can be fabricated translucent with the remainder opaque. Portions 10A and 10B could be fabricated as translucent polycarbonate or any other well known materials while portion 10C is opaque, to reduce the amount of light reaching the distal tip of insert 10. Conversely, portion 10C may be fabricated as translucent and portions 10A and 10B can be fabricated as opaque. Additionally, as shown in FIG. 11, fiber optic bundle FO can be laid in a portion of the insert shell 10A that is then conjoined with portion 10B to form an insert. The fiber optic bundle would allow the light transmission to flow from the remote lamp to the distal end of the insert system 1. Other arrangements may be derived from this disclosure without departing from the spirit of this disclosure or the invention disclosed herein.

Figure 12:
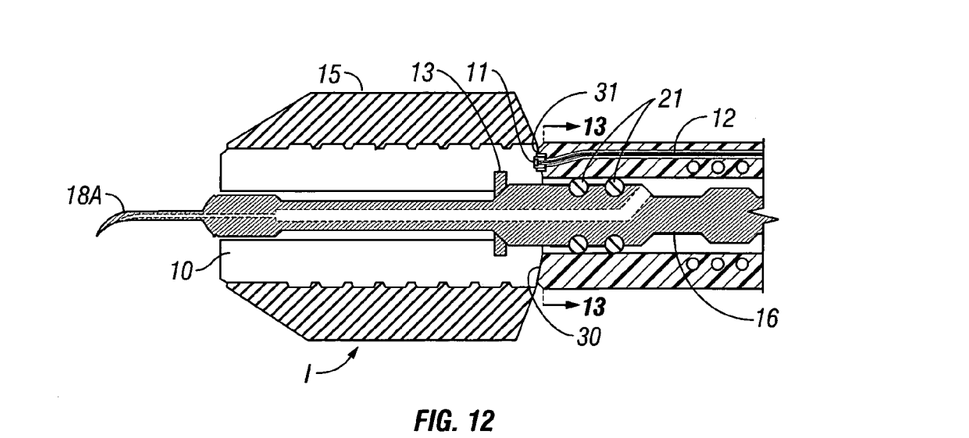
FIG. 12 is a cross-sectional side view of an alternative bayonet light connector having a male and a female connector.

Another embodiment permitting the connection of the fiber optic bundle FO through a bayonet connection 12 in handpiece H to a female receptacle 11 in insert 10 is disclosed in FIG. 12. Insert 10 (shown without a velocity transducer 16) is fashioned with female receptacle 11, which mates with male bayonet end 12 of the fiber optic bundle FO. Light is transmitted through the fiber optic cabling to the insert after handpiece end 31 is brought into mating arrangement with the proximal surface 30 of insert body 10.

Figure 13:
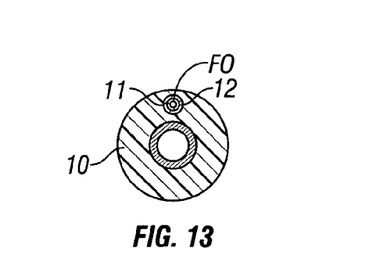
FIG. 13 is a cross-sectional end view of the alternative bayonet light connector of FIG. 12.

FIG. 13 is a partial end view of bayonet end 12 of the fiber optic FO cabling showing the relative location of the bayonet with the central core of the handpiece H. The interior of said bayonet connection 12 is filled with the terminus ends of the fiber optic cable fibers.

Figure 14:
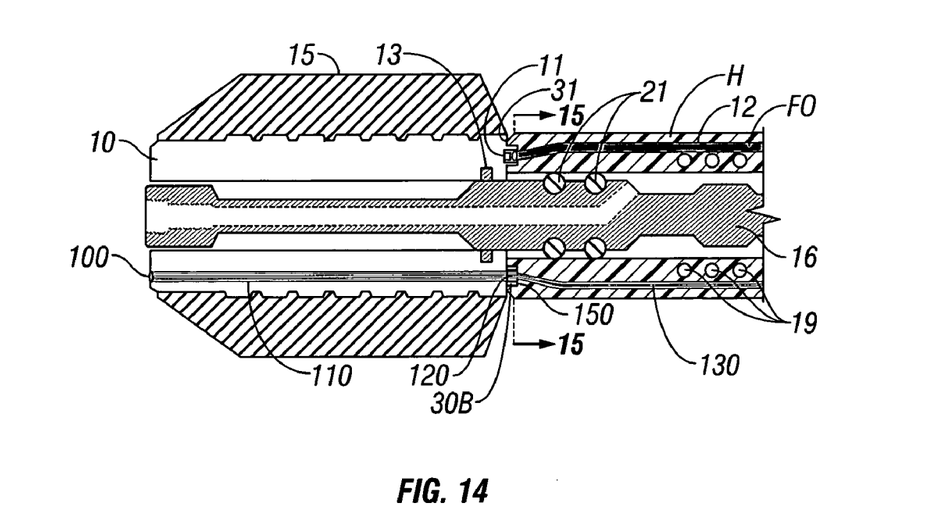
FIG. 14 is a cross-sectional side view of an alternative embodiment of a lens system mounted in the grip system of the present invention to permit the transmission of images of the work surface to a remotely located camera or video display system.

FIG. 14 is a cross-sectional view of an alternative embodiment of the lighted ultrasonic handpiece and grip system with camera lens and optical pathway. As can be appreciated, mounting a camera lens system 100 and connecting such camera lens through a return fiber optic cable bundle 110 permits the hygienist to view the area around the tip on a large screen. Since the lighting provided is adequate to illuminate the work area, the hygienist can record or permit other dental health care providers to view the scaling activity and to view the health of the gums and teeth adjacent the dental scaling tip. Utilizing the system as an ultrasonically driven scalpel would permit the surgeon to permit colleagues to view the incision being made in real time at the tip of the scalpel.

FIG. 14 discloses a cross-sectional view of the grip assembly providing a male-female bayonet connection (11, 12) for the fiber optic light guide FO into the translucent grip body 10 and a fiber optic link bayonet connection 120-30B to the camera lens 100 and integrated fiber optic fiber or endoscopic tubing 110 disposed in grip 10, providing a connector 120 to convey images obtained by the lens 100 from the space adjacent the distal end of grip 10 to the fiber optic bundle 130 for processing by the imaging portion of the camera contained within the remote control device not shown. The provision of a CCD or other optical device to capture the image provided by a remote lens/fiber optic cable system is well known technology to those skilled in the art of making and using dental and medical equipment.

Figure 15:
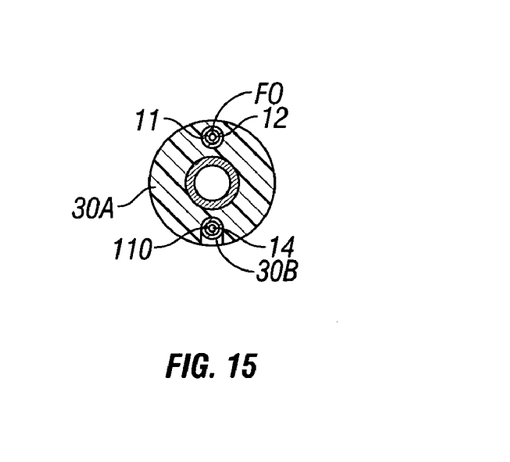
FIG. 15 is a cross-sectional end view of an alternative embodiment of the lens support system of FIG. 14 above.

FIG. 15 is an end cross-sectional view of the light providing handle H providing bayonet connections for both the light delivering fiber optic FO bundle (11–12) to the grip system and the lens providing imaging (100-110-30B). When connected to the grip, the light providing handle H introduces an appropriate level and frequency of light into grip 10 for illumination of the distal end of the grip and the camera lens 100 obtains and permits an image to be returned through grip 10 in fiber optic cable or endoscopic tube 110 to connector 120 which mates with receptacle 30B which is connected to fiber optic cable 130 for return to the control box containing the image processor. A variety of viewing angles may be chosen from 0° (straight ahead) to 90° (at a right angle to the longitudinal axis of the insert).

In the embodiment of tubing 110 inserted into grip 10, connector 120 mates with the tube through connector 30B in the light ring 30A. Other methods of providing a path to and a connection with the fiber optic cabling FO can be provided without departing from the spirit or intent of the present disclosure.

Figure 16:
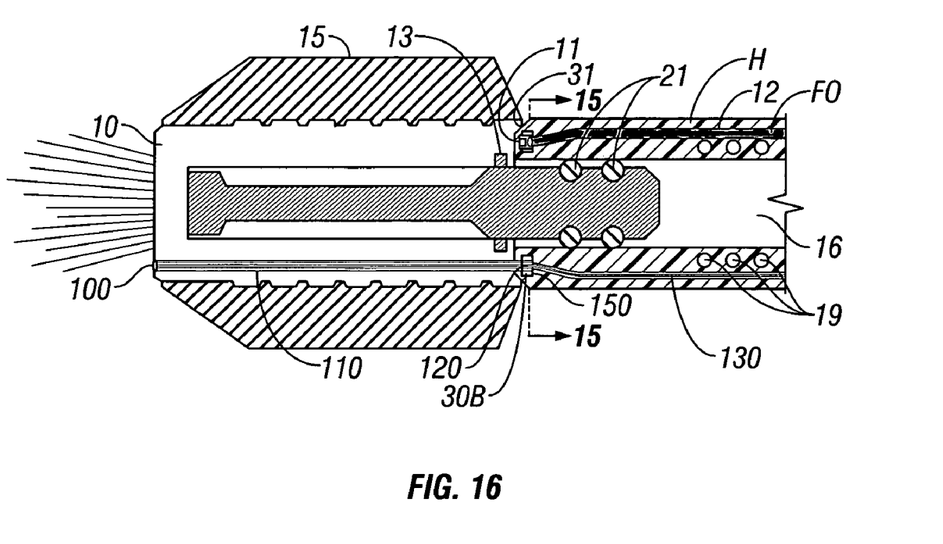
FIG. 16 is a cross-sectional view of a camera lens snub assembly which allows the camera to be used at the end of a standard ultrasonic dental appliance for recording or viewing the work without being encumbered by the tip system.

Further, it may be useful to provide a lighted camera which may be readily held by the hygienist for viewing the gums, teeth or other portions of the mouth either before or after the procedure. FIG. 16 discloses an alternative embodiment of the present lighted handpiece which provides a lighted insert 10, with sheath 15, inserted in handpiece H of a standard ultrasonic scaler, but which only provides a light path and camera lens and optical system for viewing the work area unimpeded by the presence of the tip system. The grip 10 is closed at its distal end providing sufficient light for the camera lens 100 to gather an unobstructed view of the gums which is returned to the optical system through fiber optic cabling 110 to the handpiece and its fiber optic cabling 130.

Figure 17:
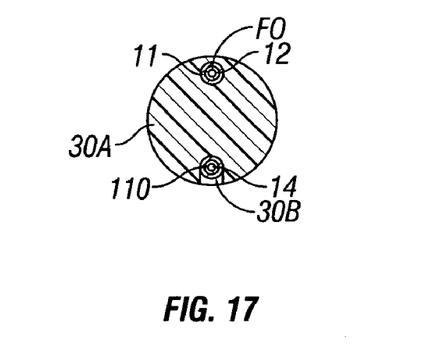
FIG. 17 is a cross-sectional end view of an alternative embodiment of the camera lens snub assembly of FIG. 16 above.

FIG. 17 is a cross-sectional end view of an alternative embodiment of the camera lens snub assembly of FIG. 16. Light ring 30A is a solid piece which provides a light path and camera lens and optical system for viewing the work area unimpeded by the presence of the tip system.

One skilled in the art will realize that the embodiments disclosed are illustrative and that the scope and content of the invention is to be determined by the scope of the claims.

The invention claimed is:

1. An ultrasonic apparatus comprising:
   a tip;
   a velocity transducer connected to the tip;
   a light guide comprising an annular translucent insert disposed on the velocity transducer;
   an ultrasonic driver connected to the velocity transducer;
   a light source terminus abutting the translucent insert;
   a light transmission cable connected to the light source terminus;
   a light source providing illumination through the light transmission cable to the light source terminus; and
   a resilient opaque sheath over the translucent insert forming a grip body.

2. The ultrasonic apparatus of claim 1 wherein the insert provides one or more longitudinal translucent paths through the grip body.

3. The ultrasonic apparatus of claim 1 wherein the insert is formed with one or more fiber optic bundles running therethrough to permit the transmission of light.

4. The ultrasonic apparatus of claim 1 wherein the insert provides external ridges to inhibit movement of the opaque sheath positioned thereon.

5. The ultrasonic apparatus of claim 1 wherein the insert provides an indented external surface to restrain movement of the opaque sheath retained thereon.

6. The ultrasonic apparatus of claim 1 wherein the ultrasonically-driven tip is a dental scaler.

7. The ultrasonic apparatus of claim 1 wherein the ultrasonically-driven tip is a scalpel.

8. The ultrasonic apparatus of claim 1 wherein the ultrasonic driver is a magnetostrictive stack device.

9. The ultrasonic apparatus of claim 1 wherein the ultrasonic driver is a piezoelectric crystal device.

10. The ultrasonic apparatus of claim 1 wherein the light source terminus is an at least partially translucent ring affixed on a distal end of a fiber optic light transmission cable.

11. The ultrasonic apparatus of claim 1 wherein the light source terminus is an at least partially translucent ring affixed on a distal end of a liquid light transmission cable.

12. The ultrasonic apparatus of claim 1 wherein the light source is switchable on and off independently of power to the ultrasonic driver.

13. The ultrasonic apparatus of claim 1 wherein the light source is adjustably regulated to provide differing amounts of light at a distal end of the grip body.

14. The ultrasonic apparatus of claim 1 wherein the sheath is elastomeric and cylindrically shaped.

15. The ultrasonic apparatus of claim 1 wherein the sheath is elastomeric and generally triangular shaped.

16. The ultrasonic apparatus of claim 1 wherein the sheath is elastomeric and arcuate shaped providing a smaller diameter in the middle of the sheath than at either end of the grip body to facilitate gripping.

17. The ultrasonic apparatus of claim 1 wherein the velocity transducer is optically opaque.

18. The ultrasonic apparatus of claim 1 wherein the light source is a high intensity light selected from incandescent filament lamps, arc lamps, or electric discharge lamps.

19. The ultrasonic apparatus of claim 18 further comprising a temperature sensor to disconnect the light source if heat above a preset level is detected in the light source.

20. The ultrasonic apparatus of claim 18 further comprising a timer to automatically disconnect the light source a fixed time after ultrasonic power is reduced to standby position.

21. A lighted ultrasonic handpiece comprising:
a light guide comprising an at least partially translucent annular insert disposed on an ultrasonic velocity transducer connected to a tip and energized by an ultrasonic generator in said handpiece;
a light source terminus abutting said translucent insert providing illumination through the insert to a distal end of the insert adjacent the tip;
a light cable connected to said light source terminus providing illumination from a remote source to the light source terminus; and
a resilient opaque sheath covering said translucent insert and forming a grip thereby preventing the light from leaving the translucent insert at any position except at the distal end.

22. The handpiece of claim 21 wherein the translucent insert is made from two halves of a polycarbonate material joined together to retain the ultrasonic velocity transducer.

23. The handpiece of claim 22 wherein the polycarbonate material is ultrasonically welded together.

24. The handpiece of claim 21 wherein the light source terminus is a circular translucent block providing illumination to an adjacent end of the translucent insert.

25. The handpiece of claim 24 wherein the circular translucent block is affixed to the end of the light cable.

26. An ultrasonic handpiece grip system comprising:
an interchangeable, user-selected, molded body having a longitudinal passage therethrough; and,
a light guide comprising an annular translucent insert disposed on a velocity transducer and providing an exterior surface for engaging the molded body within the longitudinal passage and permitting passage of light through the molded body to a distal end of the molded body to illuminate an area adjacent a distal tip of the grip.

27. The ultrasonic handpiece grip system of claim 26 wherein the molded body is selectively colored for visually distinguishing the ultrasonic handpiece grip system from a similar handpiece grip system having a differing colored exterior surface.

28. The ultrasonic handpiece grip system of claim 26 wherein the molded body is elastomeric and made from a variety of specific durometer materials.

29. The ultrasonic handpiece grip system of claim 28 wherein the molded elastomeric body is made from silicon rubber.

30. The ultrasonic handpiece grip system of claim 28 wherein an exterior surface of the molded elastomeric body is cylindrical.

31. The ultrasonic handpiece grip system of claim 28 wherein an exterior surface of the molded elastomeric body is ovate spheroidal.

32. The ultrasonic handpiece grip system of claim 28 wherein an exterior surface of the molded elastomeric body is triangular.

33. The ultrasonic handpiece grip system of claim 28 wherein an exterior surface of the molded elastomeric body is striated.

34. The ultrasonic handpiece grip system of claim 28 wherein an exterior surface of the molded elastomeric body is tapered from a larger proximal end to a smaller distal end.

35. The ultrasonic handpiece grip system of claim 28 wherein an exterior surface of the molded elastomeric body is tapered from a larger distal end to a smaller proximal end.

36. The ultrasonic handpiece grip system of claim 28 wherein an exterior surface of the molded elastomeric body has an outer diameter of between about 0.3 in to about 0.7 in.

37. The apparatus of any one of claims 1, 21 or 26 wherein the translucent insert further provides a camera lens on its distal end optically connected through the translucent insert to its proximal end.

38. The ultrasonic handpiece grip system of claim 37 wherein an optical connection in the translucent insert and a second fiber optic bundle are mated in a handpiece to permit transmission of images from the camera lens to a remote image processing systeim.

* * * * *

UNITED STATES PATENT AND TRADEMARK OFFICE
CERTIFICATE OF CORRECTION

PATENT NO. : 7,150,629 B2
APPLICATION NO. : 10/249165
DATED : December 19, 2006
INVENTOR(S) : James Feine Page 1 of 1

It is certified that error appears in the above-identified patent and that said Letters Patent is hereby corrected as shown below:

Column 2, line 45, "generator driving a said handpiece" should read --generator in said handpiece--.

Column 2, line 54, "slip" should read --slipped--.

Column 4, line 47, "0-rings" should read --O-rings--.

Column 6, line 8, "opticail" should read --optically--.

Column 8, line 42, in claim 7, "sonically- driven" should read --sonically-driven--.

Column 10, line 45, in claim 38, "systeim" should read --system--.

Signed and Sealed this

Thirteenth Day of March, 2007

JON W. DUDAS
*Director of the United States Patent and Trademark Office*